(12) United States Patent
Kim et al.

(10) Patent No.: US 10,024,816 B2
(45) Date of Patent: Jul. 17, 2018

(54) PERSONAL BLOOD GLUCOSE METER AND ABNORMAL MEASUREMENT DETECTION METHOD USING SAME

(71) Applicant: I-SENS, INC., Seoul (KR)

(72) Inventors: Tae Eun Kim, Seoul (KR); Myeong-Ho Lee, Seoul (KR); Min Woo Suh, Seoul (KR); Geun Sig Cha, Seoul (KR); Hakhyum Nam, Seoul (KR)

(73) Assignee: I-SENS, Inc., Seoul (KR)

( * ) Notice: Subject to any disclaimer, the term of this patent is extended or adjusted under 35 U.S.C. 154(b) by 365 days.

(21) Appl. No.: 14/357,177

(22) PCT Filed: Oct. 9, 2012

(86) PCT No.: PCT/KR2012/008174
§ 371 (c)(1),
(2) Date: May 8, 2014

(87) PCT Pub. No.: WO2013/069895
PCT Pub. Date: May 16, 2013

(65) Prior Publication Data
US 2014/0299487 A1 Oct. 9, 2014

(30) Foreign Application Priority Data
Nov. 11, 2011 (KR) .................. 10-2011-0117618

(51) Int. Cl.
*G01N 27/327* (2006.01)
(52) U.S. Cl.
CPC ..... *G01N 27/3274* (2013.01); *G01N 27/3271* (2013.01); *G01N 27/3273* (2013.01)

(58) Field of Classification Search
CPC ......... G01N 27/327–27/3274; G01N 27/4175; G01N 27/48; G01N 27/26; G01N 33/487; G01N 33/49; C12Q 1/00; C12Q 1/001; C12Q 1/004; C12Q 1/005; C12Q 1/006;
(Continued)

(56) References Cited

U.S. PATENT DOCUMENTS

| 6,733,655 | B1 * | 5/2004 | Davies ................... C12Q 1/001 205/775 |
| 7,220,573 | B2 | 5/2007 | Shea et al. |
| 8,367,023 | B2 | 2/2013 | Bae et al. |

(Continued)

OTHER PUBLICATIONS

International Search Report from PCT Application No. PCT/KR2012/008174, dated Mar. 22, 2013.

*Primary Examiner* — Maris R Kessel
(74) *Attorney, Agent, or Firm* — Klarquist Sparkman, LLP (57) ABSTRACT

A personal blood glucose meter and a method for sensing abnormal measurement using the same are disclosed. A personal blood glucose meter includes: a sensor strip for collecting and applying a blood sample, wherein the sensor strip includes a reagent; an electrode unit including a plurality of electrodes for receiving the blood sample from the sensor strip to generate electric current based on potential differences; an MCU for measuring currents value generated from the electrode unit to determine whether a glucose value of the blood sample is normal or abnormal; a potential supply unit for applying a predetermined potential to the electrode unit; and a display unit displaying resultant output from the MCU.

5 Claims, 5 Drawing Sheets

(58) Field of Classification Search
CPC .... C12Q 1/26; C12Q 1/34; C12Q 1/54; A61B 5/14532; A61B 5/14535; A61B 5/14536
See application file for complete search history.

(56) References Cited

U.S. PATENT DOCUMENTS

| | | |
|---|---|---|
| 2002/0175075 A1 | 11/2002 | Deng et al. |
| 2003/0094383 A1* | 5/2003 | Kermani ............ G01N 27/3273 205/777.5 |
| 2004/0154932 A1 | 8/2004 | Deng et al. |
| 2006/0175205 A1* | 8/2006 | Cui ........................ C12Q 1/006 205/777.5 |
| 2009/0205976 A1 | 8/2009 | Yoshioka et al. |

* cited by examiner

PERSONAL BLOOD GLUCOSE METER AND ABNORMAL MEASUREMENT DETECTION METHOD USING SAME

CROSS REFERENCE TO RELATED APPLICATIONS

This is the U.S. National Stage of International Application No. PCT/KR2012/008174, filed Oct. 9, 2012, which was published in English under PCT Article 21(2), which in turn claims the benefit of KR Application No. 10-2011-0117618, filed Nov. 11, 2011, which is incorporated by reference herein in its entirety.

BACKGROUND OF THE INVENTION

1. Field of the Invention

The present disclosure relates to a method for sensing whether blood glucose is normal or abnormal by self-monitoring, and more particularly, to a personal blood glucose meter capable of sensing abnormal measurement by controlling electric potential applied to an working electrode and a flow sensing electrode and to a method for sensing abnormal measurement using the same.

2. Description of the Related Art

Recently, for diagnosing and preventing diabetes, the necessity to periodically measure the amount of glucose in blood (blood glucose) has been increased. Such blood glucose may be easily measured by using a hand-carried potable measuring instrument, and specifically, may be easily measured by using a biosensor in a strip form personally. An working principle of the biosensor for measuring blood glucose is based on a colorimetric method or an electrochemical method.

Among the methods, the electrochemical method is described by the following Reaction Formula 1, and the most significant feature thereof is to use an electron transfer mediator. The electron transfer mediator includes: ferrocene; ferrocene derivatives; quinines, quinone derivatives; organic and inorganic substance containing transition metal (such as hexa-amine ruthenium, a polymer containing osmium, potassium ferricyanide, etc.); and an electron transfer organic substance such as an organic conducting salt and violegen.

Reaction Formula 1

(in the Formula, GOx represents glucose oxidase, and GOx-FAD and GOx-FADH$_2$ respectively represent the oxidized state and the reduced state of FAD (flavin adenine dinucleotide) that is an active site of the glucose oxidase)

As shown in Reaction Formula 1, (1) firstly, glucose in blood is oxidized into gluconic acid by catalysis of glucose oxidase. FAD, which is the active site of the glucose oxidase, is reduced to FADH$_2$. (2) Thereafter, the reduced FADH$_2$ is oxidized into FAD through oxidation-reduction reaction with an electron transfer mediator, and the electron transfer mediator is reduced. The formed electron transfer mediator in a reduced state is diffused to an electrode surface. Hereat, concentration of blood glucose is measured by measuring current generated by applying oxidation potential of the electronic transfer mediator in a reduced state at an working electrode surface.

A biosensor based on the electrochemical method described above as an working principle is referred to as an electrochemical biosensor. Unlike related art biosensors using the colorimetric method, such an electrochemical biosensor has an advantage that it is possible to use a sample without an additional pretreatment although the sample is turbid.

Such an electrochemical biosensor is generally and conveniently used to monitor and control an amount of blood glucose, but accuracy of the sensor is greatly affected by various interference substances such as ascorbic acid, acetaminophen, and uric acid which are present in a blood sample and are easily oxidized.

In addition, another serious error is caused by hematocrit (a degree of a ratio of hematocrit in blood). In people who regularly measure his blood glucose levels using a disposable biosensor strip, the biosensor greatly affected by a hematocrit level causes erroneous determination in the measurement result. As a result, even a risk to life of people using the biosensor may be caused.

In the related art, several methods have been proposed as a method for decreasing an influence of hematocrit in a biosensor, for example, a method of additionally separating red blood cells; a method of applying a layer for removing red blood cells onto a reagent layer (JP 1134461, JP 2000338076, and U.S. Pat. No. 5,658,444); a method of using a sensing film including a silica filler which is screen-printable and has an integrated reagent/blood cell separation function (U.S. Pat. No. 6,241,862 B1); and a correction method of mathematically processing (chemometric method) a result obtained by applying application potential twice (the double excitation potentials) (WO 01/57510 A2).

However, the methods described above may cause great loss of a reagent in an extra step or in printing the reagent layer, in the manufacturing process, and it is difficult to simply apply a reagent mixture onto an working electrode.

Obtaining a rapid response time accurately with a small amount of samples, when using a biosensor, maximized user's convenience and is thus a very important. Particularly, when using a small amount of samples of 1 μl or less, preferably samples of 0.5 μl or less, more preferably samples of 0.3 μl or less, it is possible to collect and measure blood at a substitute site such as a forearm, thereby minimizing pain of a patient from measuring blood glucose.

The time to obtain a response for the measurement result is preferably within 10 seconds, more preferably within 5 seconds if possible, and further most preferably about a time t1 if possible, but it is almost impossible to achieve such an object with a currently known technique.

A personal blood glucose meter in an electrochemical-measure manner has been developed and used to overcome such a problem, but such a personal blood glucose meter in an electrochemical-measure manner calculates a blood glucose value by measuring current generated by a potential difference between an working electrode and an auxiliary electrode of a strip. However, recently, a third electrode or more electrodes (referred to as the third electrode as a common name) in addition to two electrodes is positioned on a strip to accurately measure a blood glucose value.

However, in the strip having two or more electrodes, the auxiliary electrode may not play the role due to breakdown of the auxiliary electrode, defect of a strip connector, or blood clotting of the connector caused by user's carelessness. At this time, the third electrode plays a role of the auxiliary electrode to generate an undesired potential difference, or to cause a strip to be misidentified as a strip in which arrangement between the working electrode and the auxiliary electrode is completely different. Accordingly, there is a problem that the personal blood glucose meter may inform a user of an inaccurate measured value.

SUMMARY OF THE INVENTION

Embodiments of the present invention are directed to provide a personal blood glucose meter and a method for sensing abnormal measurement using the same, capable of solving such typical problems that a counter electrode may not work well due to breakdown of a counter electrode, defect of a strip connector, or blood clotting of a connector caused by user's carelessness in a strip having two or more electrodes in a personal blood glucose meter, in this case an auxiliary electrode plays a role of the counter electrode to generate an undesired potential difference or to cause a strip to be misidentified as a strip in which an working electrode and a counter electrode are totally different in structure.

According to an aspect of the present invention, there is provided a personal blood glucose meter according to an embodiment of the present invention includes: a sensor strip collecting and applying a blood sample, wherein the sensor strip includes a reagent; an electrode unit including a plurality of electrodes receiving the blood sample from the sensor strip to generate current based on potential differences; an MCU measuring currents value generated from the electrode unit to determine whether a glucose value of the blood sample is normal or abnormal; a potential supply unit for applying a predetermined potential to the electrode unit; and a display unit displaying resultant output from the MCU.

The electrode unit includes: a flow sensing electrode for receiving the blood sample to generate first potential; an auxiliary electrode having a ground function; and a working electrode for receiving the blood sample to generate second potential.

The MCU measures current values of the working electrode and the flow sensing electrode of the electrode unit and compares the current value with a predetermined current value to determine whether the blood glucose value is normal or abnormal.

The MCU further comprises a determination unit comparing a current value based on the potential difference with the predetermined current value, and transmitting an error message to the display when the measured current value is lower than the predetermined current value.

To solve the problem described above, the method for sensing abnormality of a personal blood glucose meter according to an embodiment of the present invention includes: applying predetermined potential from a potential supply unit to a working electrode and a flow sensing electrode provided in the personal blood glucose meter; applying blood sample to the working electrodes and the flow sensing electrode; turning off the predetermined potential supplied from the potential supply unit through MCU when the blood sample is detected at the working electrode; applying the predetermined potential to the working electrode and the flow sensing electrode with time interval after a predetermined time from the applying of the blood sample, and measuring current values of the working electrode at MCU; and comparing the current value measured with the predetermined current value to determine whether the personal blood glucose meter is in normal or abnormal operating condition.

The measuring includes: a first step of applying a predetermined potential to the working electrode and the flow sensing electrode; a second step of turning off the applied predetermined potential of the working electrode for an interval of t1 from the time when the intake of blood sample at the working electrode is detected; a third step of turning off the applied predetermined potential of the flow sensing electrode when the blood sample is sensed at the flow sensing electrode; a forth step of applying the predetermined potential to the working electrode following the second step; a fifth step of applying the predetermined potential to the flow sensing electrode after measuring the current value from the working electrode; and a sixth step of measuring the current value from the working electrode after the fifth step.

According to the present invention, it is possible to prevent claims from users beforehand wherein, the claims occur in the case when blood clots at a counter pin of a connector of a personal blood glucose meter due to user's carelessness. Also, counter breakdown or connector defect of a strip, and connector defect of a personal blood glucose meter are determined and displayed as an error, thereby preventing an erroneously measured value from being delivered to a user in advance. Therefore, the present invention has an effect of preventing a medical accident due to the erroneously measured value.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Specific structural or functional explanations for embodiments according to the inventive concept which are disclosed in this specification or application are merely provided for the purpose of illustrating the embodiments according to the inventive concept. Thus, the embodiments according to the inventive concept may be implemented in various forms and are not construed as being limited to the embodiments described in this specification or application.

The embodiments according to this inventive concept may be variously modified and may have multiple forms. Thus, specific embodiments are illustrated in the drawings or described in detail in this specification or application.

However, this is not intended to limit the embodiments according to the inventive concept as the specific disclosed forms; rather it should be understood that all of variations, equivalents or substitutes contained in the concept and technical scope of the present invention are also included.

The terms 'first' and/or 'second' may be used to describe various elements, however, the elements should not be limited by these terms. These terms are merely used for the purpose of discriminating one element from another element, and, for example, the first element may be designated as the second element, and vice versa, without departing from the spirit or scope of the present invention.

When one element is referred to as being 'connected' or 'coupled' to another element, it should be understood that the former may be directly connected or coupled to the latter, but connected or coupled to the latter via an intervening element. On the contrary, when one element is referred to as being 'directly connected' or 'directly coupled' to another element, it should be understood that the former is connected to the latter without an intervening element therebetween. Other expressions for describing the positional relationship between elements, that is, "between", "directly between" or "adjacent to" or "directly adjacent to" should be interpreted in the same manner as above.

Terms used herein are merely provided for illustration of specific embodiments, and not limited to the present invention. A singular form, otherwise indicated, include a plural form. Herein, the term "comprise" or "have" intends to mean that there may be specified features, numerals, steps, workings, elements, parts, or combinations thereof, not excluding the possibility of the presence or addition of the specified features, numerals, steps, workings, elements, parts, or combinations thereof.

Otherwise indicated herein, all the terms used herein, which include technical or scientific terms, may have the same meaning that is generally understood by a person skilled in the art. In general, the terms defined in the dictionary should be considered to have the same meaning as the contextual meaning of the related art, and, unless clearly defined herein, should not be understood abnormally or excessively formal meaning.

Hereinafter, specific embodiments of the present invention will be described in detail with reference to the accompanying drawings.

Figure 1:
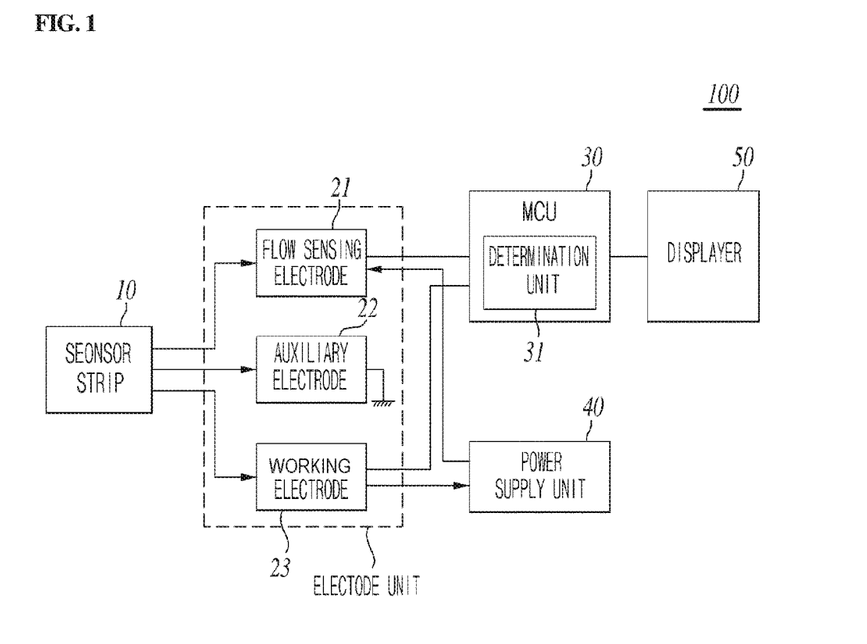
FIG. 1 is a block diagram illustrating a personal blood glucose meter according to an embodiment of the present invention.
Figure 2:
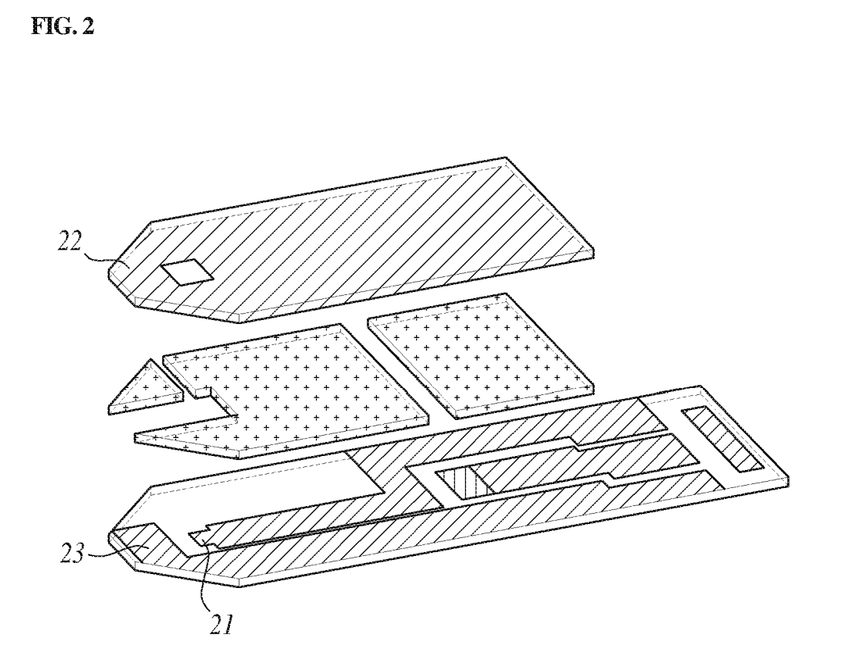
FIG. 2 is an exemplary diagram illustrating a facing-type strip used in the present invention.

FIG. 1 is a block diagram illustrating a personal blood glucose meter according to an embodiment of the present invention, and FIG. 2 is an exemplary diagram illustrating a facing-type strip used in the present invention.

As illustrated in FIG. 1, a personal blood glucose meter 100 of the present invention includes a sensor strip 10, an electrode unit 20, an MCU 30, a potential supply unit 40, and a displayer 50.

The sensor strip 10 collects and supplies blood of a user or the other person, and is provided with a sample therein.

More specifically, in the sensor strip 10 of the present invention, a thin layer electrochemical cell is configured by separately forming: an working electrode and an auxiliary electrode on two flat insulating plates in an electrode configuration; forming, a connection line connectable to the auxiliary electrode, on the plate on which the working electrode is formed; printing a conductive material onto a part of the connection line to be thick by a laminated structure to form a portion which is 3-dimensionally connected to the auxiliary electrode; and separating the working electrode and the auxiliary electrode formed on two flat insulating plates at a position symmetrically or asymmetrically facing each other by a pressure adhesive separation plate with a thickness of 50 to 250 μm (Reference to facing electrodes: E. K. Bauman et al., *Analytical Chemistry*, vol 37, p 1378, 1965; K. B. Oldham in "Microelectrodes: Theory and Applications," Kluwer *Academic Publishers*, 1991).

The thin layer separation plate is provided with a fine flow path through which a biological sample may be injected and retained in a measurement space formed by the working electrode and the auxiliary electrode and of which a total volume is in unit of micro-liter. In formation of electrodes, the flow sensing electrode in the thin layer separation plate is apart from the working electrode (or the auxiliary electrode) at a proper distance. Preferably, the flow sensing electrode is positioned at a distance where blood having the amount of hemocytes of 42% and treated with EDTA (ethylene diaminetetraacetic acid) reaches within about 600 ms along the fine flow path with a width of 0.5 to 2 mm and a height of 50 to 250 μm, more preferably is positioned at a distance where an EDTA-untreated sample reaches within 300 ms, and even more preferably is positioned at a distance where the sample reaches within 200 ms.

The working electrode (or the auxiliary electrode) and the flow sensing electrode formed on one substrate may form a biosensor characterized by having a configuration in which the working electrode (or the auxiliary electrode) faces the auxiliary electrode (also used as the predetermined electrode) (or the working electrode) (facing type).

The electrode unit 20 includes a plurality of electrodes 21, 22, and 23 for receiving blood sample, in which the blood and the sample are mixed, from the sensor strip 10 to generate electric current based on a potential difference.

The electrode unit 20 includes a flow sensing electrode 21 for receiving the blood sample to generate a first potential value, an auxiliary electrode 22 having a ground function, and an working electrode 23 for receiving the blood sample to generate a second potential value.

The MCU 30 measures a current value generated from the electrode unit 20 and calculates a blood glucose value. Also, the MCU 30 measures the current value again at a certain time interval, and compares the measured current value with a preset reference current value to determine whether the blood glucose is normal or abnormal. The MCU 30 further includes a determination unit 31 for comparing the current value based on the potential difference with the predetermined current value and transmitting an error message to the display when the measured current value is lower than the predetermined current value.

Figure 3:
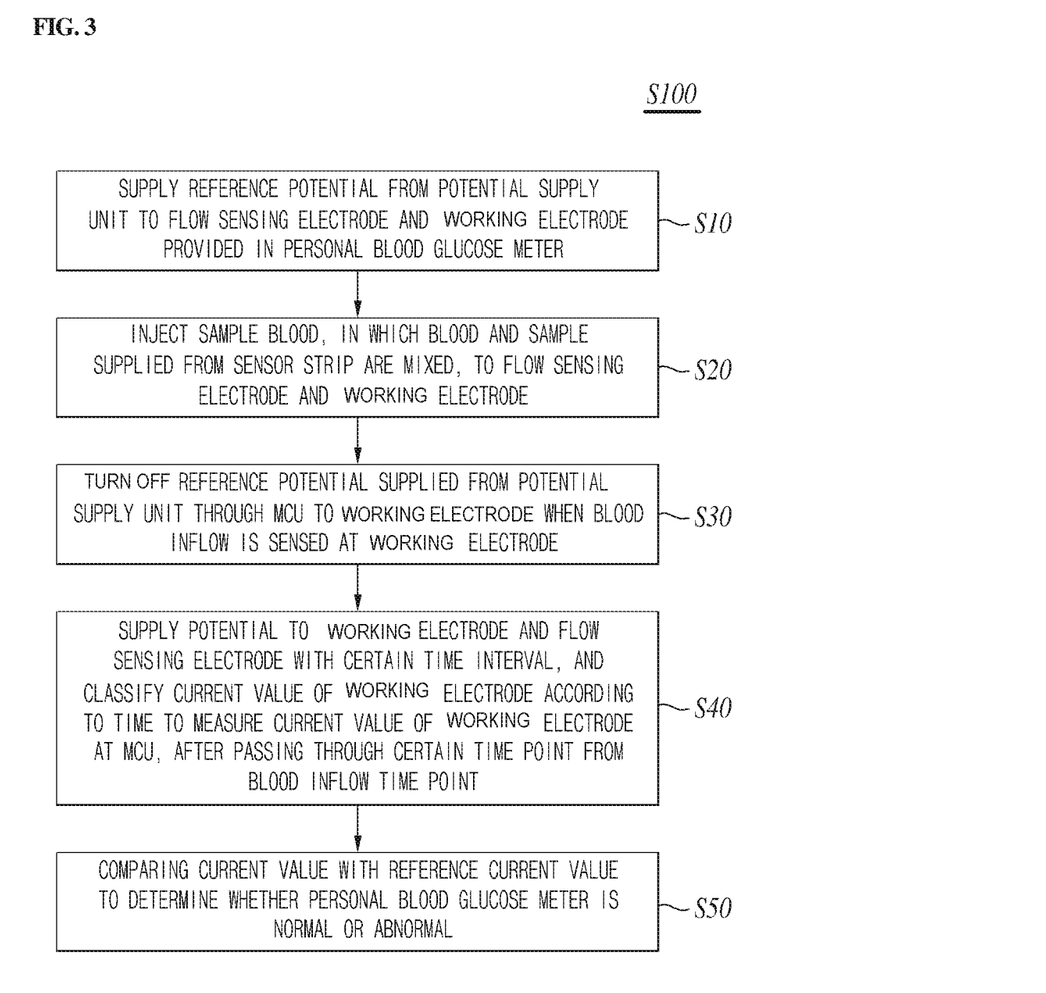
FIG. 3 is a flowchart illustrating a method for sensing abnormality of the personal blood glucose meter of the present invention.
Figure 4:
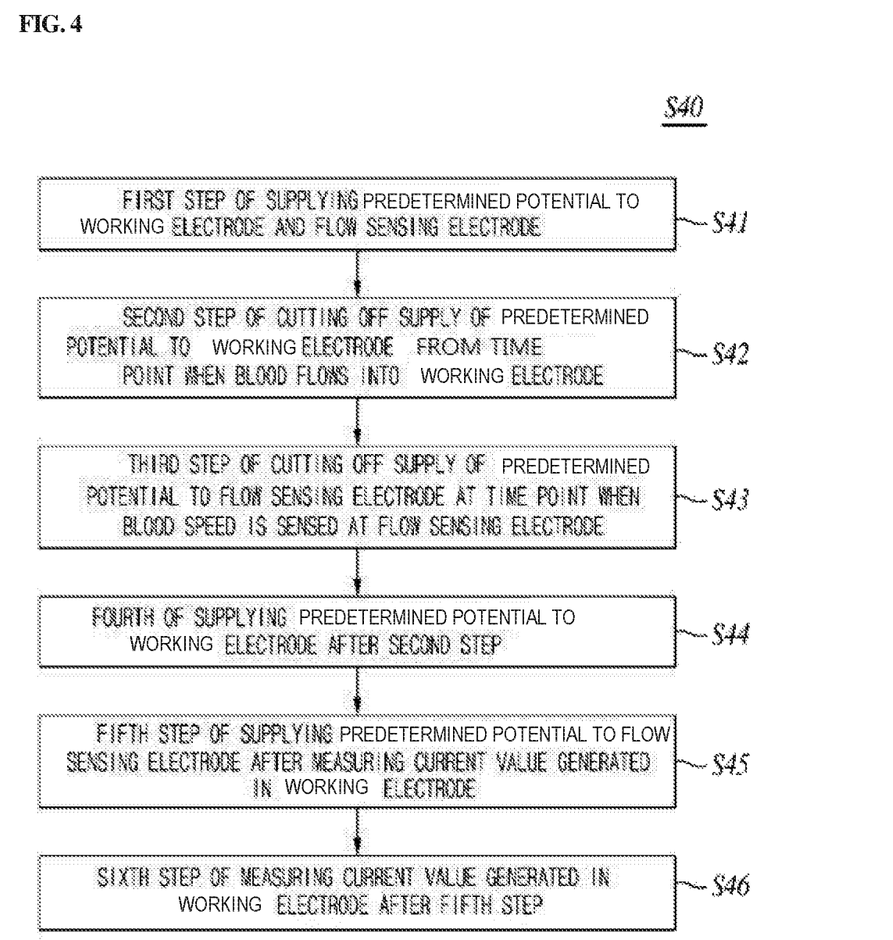
FIG. 4 is a flowchart more specifically illustrating a measuring step illustrated in FIG. 3.

FIG. 3 is a flowchart illustrating a method for sensing abnormality of a personal blood glucose meter of the present invention, and FIG. 4 is a flowchart more specifically illustrating the measuring step illustrated in FIG. 3.

As illustrated in FIG. 3, the method for sensing abnormality (S100) of a personal blood glucose meter of the present invention includes a predetermined potential applying step (S10), a blood applying step (S20), a predetermined potential apply turning-off step (S30), a measuring step (S40), and a determining step (S50).

The predetermined potential applying step (S10) may be a step of applying the predetermined potential from the potential supply unit to the flow sensing electrode and the working electrode provided in the personal blood glucose meter.

The blood applying step (S20) may be a step of applying blood sample, in which blood and a sample supplied from a sensor strip are mixed, to the flow sensing electrode and the working electrode.

The predetermined potential apply turning-off step (S30) may be a step of turning off predetermined potential supplied from the potential supply unit through the MCU when blood inflow to the working electrode is detected.

The measuring step (S40) may be a step of applying predetermined potential to the working electrode and the flow sensing electrode with an interval of time, and classifying a current value of the working electrode according to time to measure the current value at the MCU, after passing through a certain time point from the blood inflow time point.

The determining step (S50) may be a step of comparing the current value with the predetermined current value to determine whether the personal blood glucose meter is normal or abnormal.

More specifically, as illustrated in FIG. 4, the measuring step (S40) includes: a first step (S41) of applying predetermined potential to the working electrode and the flow sensing electrode; a second step (S42) of turning off the applied predetermined potential to the working electrode for time of t1 from the time point when blood flows into the working electrode; a third step (S43) of turning off the applied predetermined potential to the flow sensing electrode at the time point when a blood speed is sensed at the flow sensing electrode; a fourth step (S44) of applying the predetermined potential to the working electrode after the second step; a fifth step (S45) of applying the predetermined potential to the flow sensing electrode after a current value generated at the working electrode is measured; and a sixth step (S46) of measuring the current value generated at the working electrode after the fifth step.

Figure 5:
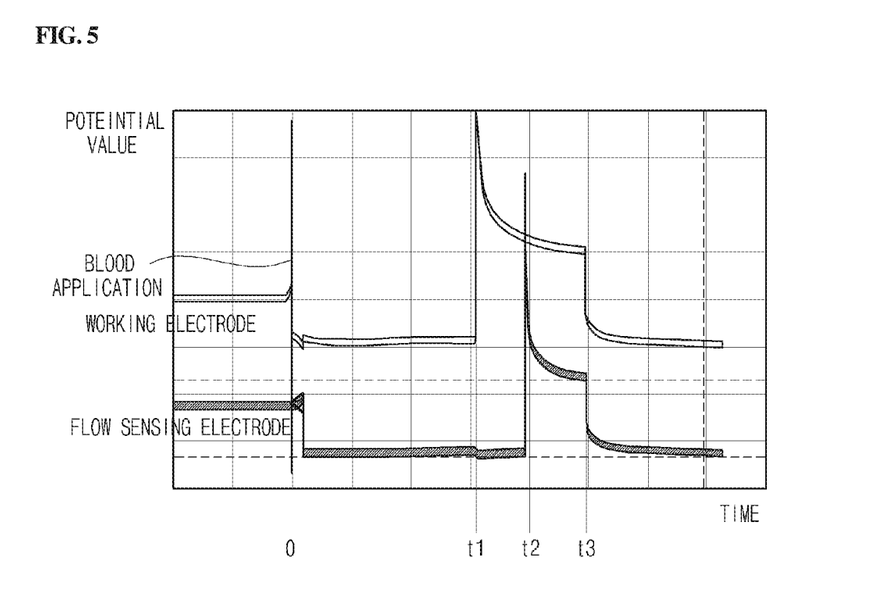
FIG. 5 is a graph illustrating potential variation of a flow sensing electrode and an working electrode at the time of normal measurement (using a normal strip sensor and a normal strip connector)
Figure 6:
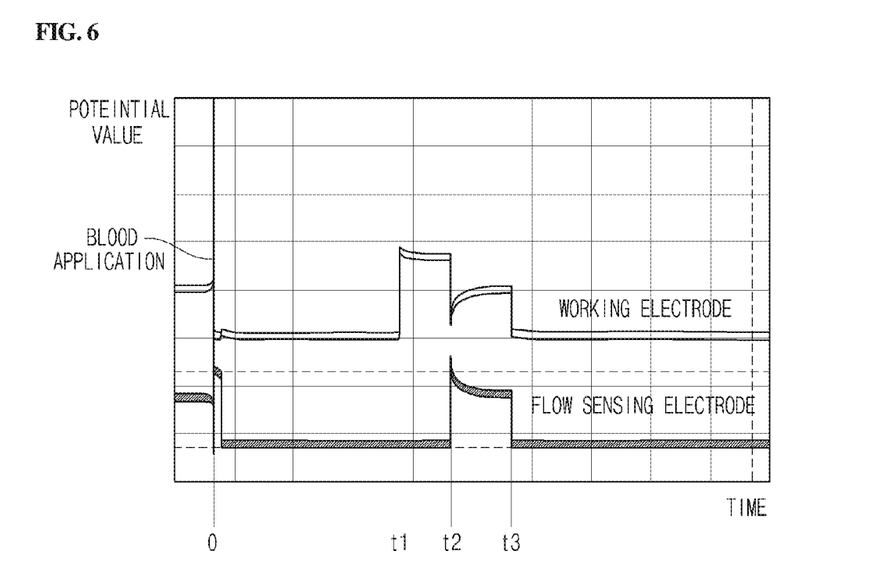
FIG. 6 is a graph illustrating potential variation of a flow sensing electrode and an working electrode at the time of abnormal measurement (using a defect strip sensor or a defect strip connector).

FIG. 5 is a graph illustrating potential variation of the flow sensing electrode and the working electrode at the time of normal measurement (using a normal strip sensor and a normal strip connector). FIG. 6 is a graph illustrating potential variation of the flow sensing electrode and the working electrode at the time of abnormal measurement (using a defect strip sensor or a defect strip connector).

FIG. 5 and FIG. 6 are materials for confirming data when a predetermined potential application time to the flow sensing electrode is increased to t0 seconds to compare data for normal measurement and data for abnormal measurement. When the normal strip and the normal connector are used, an output of the working electrode is not affected by predetermined potential applied to the flow sensing electrode, but when the defect strip or the defect connector is used, a phenomenon that the output of the working electrode has a lower predetermined potential than applied predetermined potential when the predetermined potential is applied to the flow sensing electrode.

TABLE 1

| time variation | working electrode | flow sensing electrode |
| --- | --- | --- |
| before measurement start | applying predetermined potential | applying predetermined potential |
| after measurement start (time 0) | turning off apply of predetermined potential before starting measurement | turning off applied predetermined potential after measuring a blood speed |
| from time 0 to time t1 after measurement start | turning off apply of predetermined potential | turning off apply of predetermined potential |
| from time t1 to time t2 after | applying predetermined | turning off apply of predetermined |
| measurement start measure, at time t2 | potential measuring current, calculating as blood glucose value | potential applying predetermined potential to flow detection electrode after measuring current at working electrode |
| from time t2 to time t3 after measure | applying predetermined potential | applying predetermined potential |
| measure, at time t3 | measuring electric current, determining whether normal measurement or not | applying predetermined potential |
| after measure | turning off apply of predetermined potential | turning off apply of predetermined potential |

Table 1 shows steps performed according to external variation (applying predetermined potential and turning off apply of predetermined potential) and time variation at the working electrode and the flow sensing electrode to test sensing the abnormal measurement of the personal blood glucose meter.

Referring to FIG. 5, FIG. 6, and Table 1, in a case of the normal strip, there is no significant difference between the blood glucose value measured at the time t2 and the value measured again at the time t3 after raising low voltage of the auxiliary electrode for a certain time, but in the case of the breakdown strip, there is a significant difference between the value measured at the time t2 and the normal value, and the current value measured at the time t3 has a negative value.

The reason for this result is that because the flow sensing electrode plays a role of the auxiliary electrode when the auxiliary electrode does not play it's own role due to the reason described above, the potential difference between the working electrode and the flow sensing electrode disappears when the predetermined potential of the flow sensing electrode is raised to the predetermined potential after the time t2, and therefore an effect that the potential difference of the working electrode with respect to the auxiliary electrode disappears occurs.

Accordingly, the measurement value of the time t2 is displayed as a blood glucose value, and breakdown of the auxiliary electrode or a case where blood clots at the connector and the auxiliary electrode does not play the role is processed as an error using the measurement value at the time t3. Thus, it is possible to prevent an erroneous measurement value from being transferred to a user.

Therefore, in the present invention, when the flow sensing electrode 21 is recognized as the auxiliary electrode 22 due to various problems, the predetermined potential of the auxiliary electrode 22 is changed and the blood glucose value is measured again in a short time after completing measurement of blood glucose to determine the recognition.

When the normal strip and the normal connector are used, there is little difference between a first measured blood glucose value and a value re-measured a short time after. However, when the broken strip or the broken connector is used, the flow sensing electrode is used as the auxiliary electrode, and thereby, the predetermined potential of the auxiliary electrode is different from that of the normal strip. As a result, there is a significant difference between the first measurement value and the re-measurement value.

In order to prove this, a facing-type strip, in which the working electrode 23 and the flow sensing electrode 21 are positioned on a lower plate and the auxiliary electrode is positioned on an upper plate facing the lower plate, was used (see FIG. 2).

When an abnormal situation such as breakdown of the auxiliary electrode occurs, the flow sensing electrode 21 replaces the auxiliary electrode 22. Also, the facing-type strip takes a form of a plane-type strip, in which the working electrode 23 and the auxiliary electrode 22 are position on the same plate, and thus the abnormal measurement occurs.

Although the flow sensing electrode plays the role of the auxiliary electrode 22 by raising the predetermined potential of the flow sensing electrode 21 to the same potential as that of the working electrode 23 after the first measurement, the potential difference from the working electrode 23 disappears, and thus current is not generated.

Accordingly, when the first measurement current value is calculated as a blood glucose measurement value and the second measurement current value is not generated or becomes a negative value, it may be determined as a strip defect or a connector defect.

According to the present invention, it is possible to previously prevent claims from users generated when blood clots at the auxiliary electrode pin of a connector of a personal blood glucose meter due to user's carelessness. Also, counter breakdown or a connector defect of a strip, and a connector defect of a personal blood glucose meter are displayed by an error message, thereby preventing an erroneous measurement value from being transferred to a user and preventing a medical accident.

The embodiments of the present invention disclosed in the specification and the drawings are to merely present specific examples to easily explain the technical contents of the present invention and to help the present invention to be understood, and do not limit the scope of the present invention. Even in addition to the embodiments disclosed herein, it is obvious that other modified examples based on the technical idea of the present invention can be embodied by a person skilled in the art to which the present invention pertains.

What is claimed is:

1. A method for sensing abnormality of a personal blood glucose meter, the personal blood glucose meter comprising:
   a sensor strip for collecting a blood sample comprising two insulating plates facing each other and an electrode unit, wherein
   the electrode unit is coupled to the sensor strip and including a plurality of electrodes comprising a flow sensing electrode, an auxiliary electrode having a ground function, and a working electrode, wherein the working electrode and the flow sensing electrode are on one of the two insulating plates and the auxiliary electrode is on the other of the two insulating plates;
   a potential supply unit for applying potential to the electrode unit; and
   a microcontroller unit for measuring current values generated from the electrode unit to determine whether a blood glucose value of the blood sample is normal or abnormal;
   the method comprising:
   applying a first predetermined potential from the potential supply unit to the flow sensing electrode and the working electrode;
   receiving a blood sample at the working electrode and the flow sensing electrode sequentially;
   turning off the first predetermined potential supplied to the working electrode from the potential supply unit when the blood sample is detected at the working electrode, followed by turning off the first predetermined potential supplied to the flow sensing electrode when the blood sample is detected at the flow sensing electrode;
   applying a second predetermined potential to the working electrode to measure a first current value from the working electrode;
   applying a third predetermined potential to the flow sensing electrode to measure a second current value from the working electrode; and
   determining whether the personal blood glucose meter is in normal or abnormal operating condition based on the second current value.

2. The method according to claim 1, wherein the sensor strip includes a reagent.

3. The method according to claim 1, wherein the sensor strip further comprises:
   a connection line connectable to the auxiliary electrode on the insulating plate on which the working electrode is formed;
   a conductive material printed onto a part of the connection line by a laminated structure to form a portion which is 3-dimensionally connected to the auxiliary electrode; and
   a pressure adhesive separation plate with a thickness of 50 to 250 μm between the two insulating plates, which separates the working electrode and the auxiliary electrode formed on the two insulating plates at a position symmetrically or asymmetrically facing each other.

4. The method according to claim 1, wherein the flow sensing electrode is apart from the working electrode at a certain distance on the insulating plate on which the operation electrode is formed.

5. The method according to claim 1, wherein the working electrode on one insulating plate faces the auxiliary electrode.

* * * * *

UNITED STATES PATENT AND TRADEMARK OFFICE
CERTIFICATE OF CORRECTION

PATENT NO. : 10,024,816 B2
APPLICATION NO. : 14/357177
DATED : July 17, 2018
INVENTOR(S) : Kim et al.

It is certified that error appears in the above-identified patent and that said Letters Patent is hereby corrected as shown below:

On the Title Page

Item (72) Inventors:
Left column, at inventors, Line 4: "Seoul (KR); Hakhyum Nam, Seoul" should read -- Seoul (KR); Hakhyun Nam, Seoul --.

Signed and Sealed this
Fourth Day of September, 2018

Andrei Iancu
*Director of the United States Patent and Trademark Office*